United States Patent [19]

Tozier et al.

[11] Patent Number: 4,541,988

[45] Date of Patent: Sep. 17, 1985

[54] CONSTANT TEMPERATURE CATALYTIC GAS DETECTION INSTRUMENT

[75] Inventors: John E. Tozier, Wexford; Abraham Anouchi, Pittsburgh; Richard Critchlow, Cheswick, all of Pa.

[73] Assignee: Bacharach Instrument Company, Pittsburgh, Pa.

[21] Appl. No.: 560,784

[22] Filed: Dec. 13, 1983

[51] Int. Cl.⁴ ............................................. G01N 27/16
[52] U.S. Cl. ..................................... 422/94; 73/27 R; 324/65 R; 422/98
[58] Field of Search ................ 73/27 R, 204; 324/DIG. 1, 71.1, 65 R; 422/83, 94–98

[56] References Cited

U.S. PATENT DOCUMENTS

| | | | |
|---|---|---|---|
| 2,782,102 | 2/1957 | Howe | 422/96 |
| 3,429,178 | 2/1969 | Durbin | 73/27 R |
| 3,835,529 | 9/1974 | Taguchi | 29/570 |
| 3,865,550 | 2/1975 | Bott et al. | 23/232 |
| 3,886,785 | 6/1975 | Stadler et al. | 73/23 |
| 3,955,268 | 5/1976 | Chou et al. | 29/570 |
| 4,004,452 | 1/1977 | Logothetis et al. | 73/23 |
| 4,013,943 | 3/1977 | Chou et al. | 324/33 |
| 4,112,356 | 9/1978 | Toy | 324/71 |
| 4,141,243 | 2/1979 | Van Tassel et al. | 73/119 |
| 4,244,217 | 1/1981 | Ledbetter | 73/204 |
| 4,305,724 | 12/1981 | Micko | 422/96 X |
| 4,308,518 | 12/1981 | Hattori et al. | 338/34 |
| 4,338,281 | 7/1982 | Treitinger et al. | 422/98 |
| 4,444,056 | 4/1984 | Romo | 324/DIG. 1 X |

FOREIGN PATENT DOCUMENTS 2445550 4/1975 Fed. Rep. of Germany ........ 422/96
160760 2/1964 U.S.S.R. ........................ 324/DIG. 1

Primary Examiner—Hiram H. Bernstein
Assistant Examiner—Michael S. Gzybowski
Attorney, Agent, or Firm—Robert P. Hayter

[57] ABSTRACT

A constant temperature catalytic gas detection instrument (10) has a gas sensor (14) whose operating temperature is maintained within a predetermined range by a novel control circuit. The gas sensor includes a reference element (16) and an active element (18) on which a metal oxide catalyst reacts with the combustible gas. First and second driver circuits (30 and 36) are provided for presenting operating voltages to the active element (18) and the reference element (16), respectively, of the gas sensor (14). The first driver (30) controls the power to the active element (18), to maintain its temperature within a predetermined operating range. The second driver (36) responds to changes in the power through the active element (18) with respect to the current through the active element (18), causing the current in the reference element (16) to track the current in the active element (18). An indicator (38) connected between the active element (18) and the reference element (16) senses a potential difference therebetween to provide an indication of the concentration of said unknown gas.

5 Claims, 1 Drawing Figure

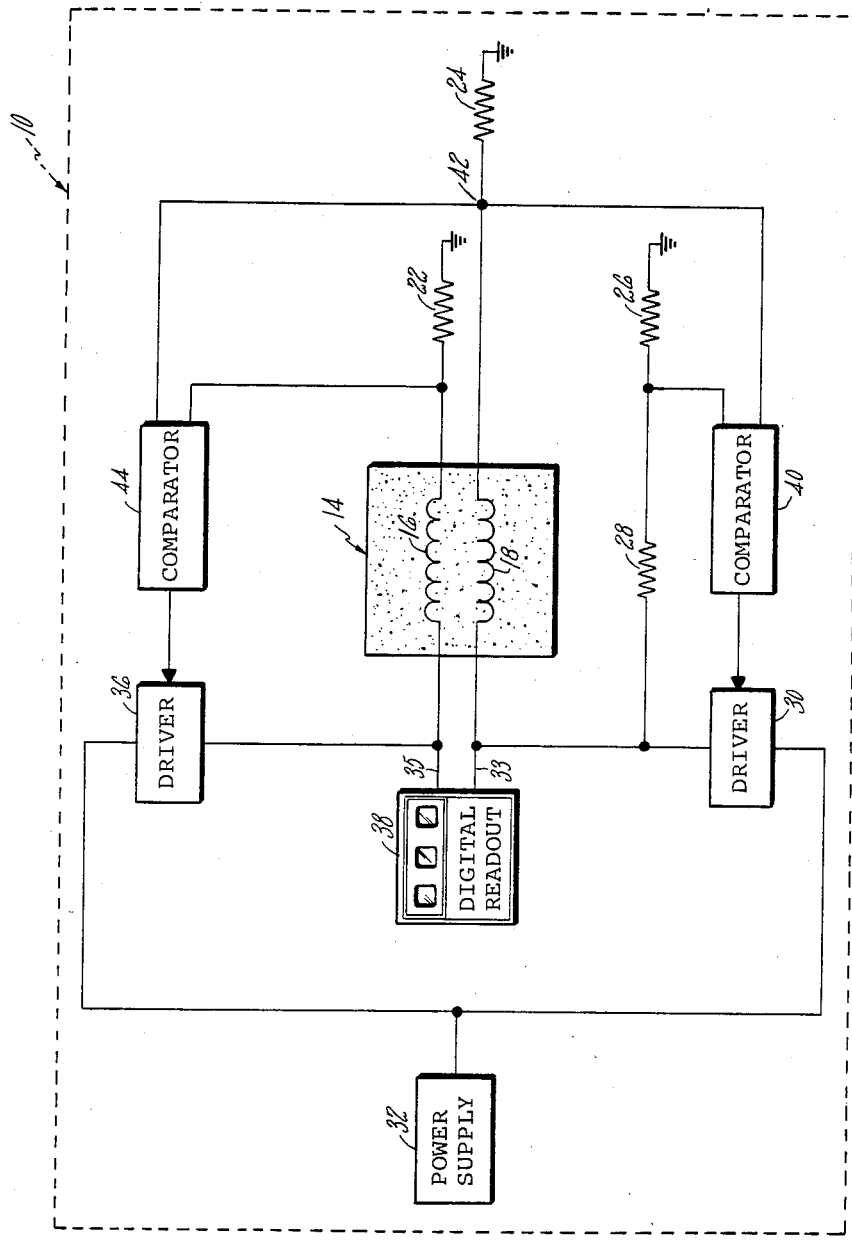

CONSTANT TEMPERATURE CATALYTIC GAS DETECTION INSTRUMENT

TECHNICAL FIELD

This invention relates to a gas detection instrument for detecting combustible gases, and more particularly, to an improved gas detection instrument having a temperature-compensation circuit used with a catalytic gas sensor to ensure the sensor operating temperature is within a predetermined range.

BACKGROUND ART

Numerous gas detection instruments are known and most include a gas sensor which responds to concentrations of a particular gas of interest. One type of gas detection instrument which includes an oxygen sensor is described in U.S. Pat. No. 3,886,785 issued June 3, 1975 to H. Stradler for "Gas Sensor and Method of Manufacture". The oxygen sensor, and its method of manufacture as described in this patent, has a sintered ceramic body of transition metal oxide with a pair of spaced-apart electrodes. As the partial pressure of oxygen in the gas being sensed varies in response to variations in the inlet air/fuel mixture ratio, the resistance of the ceramic material varies.

Another type of gas detection instrument which includes a solid state gas sensor is described in U.S. Pat. No. 4,013,943 issued Mar. 22, 1977 to J. Chau et al for "Solid State Electronic Cell Gas Sensor Head". The sensor described in this patent is capable of measuring low concentration levels of oxygen as well as up to about 20% by volume. The solid state material from which the sensor is fabricated is produced by the addition of one or more metal oxide to a nonmetal oxide. The sensor includes a collector and a heater element made from a stable metal such as platinum.

Another semiconductor-type gas sensor is described in U.S. Pat. No. 3,865,550 issued Feb. 11, 1975 to B. Bott for "Semi-Conducting Gas Sensitive Devices". This device includes a semiconductor of a first metal with at least one additional metal incorporated therein. The conductivity of the active oxide changes in response to exposure to the gas of interest.

Still another type of gas detection instrument includes a catalytic gas sensor that uses a small coil of platinum wire, or beads, which is exposed to a combustible gas. The beads have a resistance which varies upon oxidation and the change in resistance is identified and measured with a Wheatstone bridge, or similar type circuitry, to determine the amount of combustible gas which is present in a sample.

As is well known, the beads must be heated for oxidation to occur. With methane, catalytic oxidation with platinum wire begins at about 500° C. Oxidation will occur at a lower temperature if the platinum beads are finely divided. However, generally the hotter the catalyst, up to a point, the stronger the change in resistance to a given level of gas.

If the gas detection instrument is to be portable, most often one or more batteries provide the source voltage. The catalytic sensor is heated by the source voltage and the operating temperature of the platinum beads is somewhat critical in order to produce a linear output on the Wheatstone bridge circuit when exposed to a combustible gas. Linearity in the sense can be expressed as % LFL (percent of lower flammable limit) difference between a known gas sample (in % LFL) and that level depicted by the electronic network (also expressed in % LFL). Typically linearity of less or equal to about 3% is observed when beads are operated near the critical temperature for LFL ranges up to 50%.

A particular problem with many prior art gas detection instruments which use catalytic-type gas sensors incorporating an active and reference element in one arm of a Wheatstone bridge-type circuit is that the catalytic oxidation of combustible gases results in an increase in the temperature of the active element which increases its resistance. At the same time, the resistance of the reference element decreases because of a reduction caused by the drop in current that occurs when the resistance of the active element increases. Temperature rise of the active element can exceed 100° C., or more, depending on various factors, e.g., the initial temperature in the reference air, type of combustible gas, type of catalyst, energy density of coil and thermal coupling between the burning vapor and the resistive coil wire. The active element temperature also increases even if the reference element is in the opposing arm of a Wheatstone bridge-type circuit.

An adverse effect of temperature increases in the active sensor element is the potential restructuring in size of the finely divided catalytic agglomerates. This size restructuring can affect the sensitivity of the instrument. In extreme over-temperature situations, the sensor can be irreversibly damaged. For example, palladium can be irreversibly converted to palladium oxide making it useless as a catalyst.

DISCLOSURE OF INVENTION

It is an object of the present invention to provide a constant temperature catalytic gas detection instrument which is essentially immune to the detrimental effects of operational temperature excursions resulting from the catalytic oxidation of combustible gases which tend to shorten gas sensor life.

A particular advantage of the constant temperature catalytic gas detection instrument according to the present invention is that a driver means is provided to limit the power to the active element in the gas sensor in response to increased catalytic activity, such as results from the flooding of the gas sensor with a combustible gas.

Another advantage of the constant temperature catalytic gas detection instrument according to the present invention is that the power to the active element of the gas sensor is regulated to minimize temperature fluctuations which otherwise tend to degrade the gas sensor structure in the normal gas detecting mode of operation.

Yet another feature of the constant temperature catalytic gas detection instrument according to the present invention is that the temperature for the catalytic oxidation of a combustible gas can be maintained within a predetermined range, thus improving instrument linearity for more selective identification of hydrocarbon gases.

Still another advantage of the constant temperature catalytic gas detection instrument according to the present invention is that first and second drivers provide operating potential to the gas sensor from a single power supply and yet the particular operating voltage presented to the active element and the reference element of the gas sensor is varied to maintain the temperature within a predetermined range.

The foregoing and other objects features and advantages of the present invention will become more apparent from the following description of preferred embodiments and accompanying drawing.

BRIEF DESCRIPTION OF DRAWING

The drawing is a schematic illustration of an embodiment of the constant temperature catalytic gas detection instrument according to the present invention.

BEST MODE FOR CARRYING OUT THE INVENTION

Referring to the drawing, there is seen an embodiment of the constant temperature gas detection instrument according to the present invention. Gas detection instrument is generally indicated in the drawing by the numeral 10 and is often a portable gas monitoring instrument designed to provide an alarm or a visual reading, or both, indicating the concentration level of particular gases in the atmosphere. A gas sensor 14 is provided and is positioned in the gas detection instrument such that it is readily reached by the atmosphere requiring detection. Included in the gas sensor 14 is a reference element 16 and an active element 18, both of which are formed from a wire of a noble metal or a noble metal alloy that is relatively stable at operating temperature of the sensor. Platinum is one desirable material for the two elements and the wire could be wound on a mandrel to form a coil. Both the active element 18 and the reference element 16 are positioned in a spaced relationship within the gas sensor 14 which can be filled with a porous insulating material such as aluminum oxide, or the like. The reference element 16 is preferably coated with an organic titanate, or similar material, so that it does not oxidize in the presence of a combustible gas. In contrast, the active element 18 is coated with a metal oxide, such as a finely divided platinum supported by alumina or other material, which acts as a catalyst for promoting combustion of a combustible gas in air upon exposure to the gas of interest.

Because the detection of combustible gases involves the interpretation of small resistance change, a modified version of the "Wheatstone bridge" type of circuit is used as a portion of the control network for the active element 18. In the present invention a resistor 22 is connected in series to one end of the reference element 16. A resistor 24 is connected from one end of the active element 18 to ground. A resistor 26 and a resistor 28 are series connected to form a voltage divider and are connected through a first driver 30 (explained more fully hereinafter) to a power supply 32, this often being a battery in the case of a portable instrument. The power supply 32, through the first driver 30, is also connected to a lead 33 and one end of the active element 18 for supplying an operating potential thereto. The power supply 32 is also connected through a second driver 36 (also explained more fully hereinafter) to a lead 35 and thereby to the other end of the reference element 16. A digital readout 38, signal processor, or other similar device, is connected to the leads 33 and 35 for measuring potential differences between the active element 18 and the reference element 16 in response to the catalytic oxidation process.

An important feature of the temperature compensated catalytic gas sensor according to the present invention involves an active circuit which controls the resistance of the active element 18. The active element current is monitored and current changes through the reference element 16 track the current in the active element 18. A first comparator 40 is provided and it has one input connected to a voltage divider formed by the junction of resistor 26 and the resistor 28; its other input is connected to a node 42 adjacent the resistor 24 so that all of the current flowing through the active element 18, also flows through the node 42 and the resistor 24. The output from the comparator 40 is presented to the driver 30 which controls the operating voltage level presented to the active element 18. In this fashion, the resistance (i.e., temperature) of the active element is controlled as a function of values of resistors 26, 28. A second comparator 44 is provided and has one input connected to the node 42 while the other input is connected adjacent the nongrounded end of the resistor 22. The output of the second comparator 44 is presented to the driver 36 which controls the operating voltage level presented to the reference element 16. In this fashion, the current through the reference element 16 tracks the current through the active element 18.

In operation, the temperature of the active element 18 is maintained relatively constant even when subject to high concentration levels of combustible gases, ambient temperature changes, or the like. When a combustible gas contacts the gas sensor 14, catalytic oxidation on the surface of the active element 18 burns the gas and, in prior art devices, causes the resistance of the active element to increase and hence the current to decrease. In the present invention, this small change in current through the active element 18 and the node 42 is translated into a potential difference across the resistor 24. The first comparator 40 senses this small change with respect to the voltage divider formed by the resistors 26 and 28 and decreases the operating voltage potential and the current such that the ratio of the active element voltage to the active element current remains substantially constant. In this way, the operating temperature (i.e., resistance) of the active element 18 is maintained within a constant range. Accordingly, the second comparator 44 monitors the current reduction flowing through the node 42. Through the driver 36 the current in the reference element 16 is correspondingly reduced to track the current in the active element 18. Since the resistance (i.e., temperature) of the reference element 16 is not directly affected by the catalytic oxidation occurring on the active element 18, the current reduction therethrough results in a decrease in the resistance of the reference element 16, and its temperature will be reduced by a corresponding amount. Thus, the difference in resistance (which remains relatively constant) between the active element 18 when exposed to a combustible gas and the resistance reference element 16 is a measure of gas concentration. And, this potential difference between the leads 33 and 35 is used by the digital readout 38 to provide a measure of the gas concentration level.

In one test the resistance of the active element 18 was held constant to within 0.5% over a 50° C. ambient temperature change while at the same time catalytic oxidation to a level of 50% LFL methane in air occurred. This is less than a 4° C. change in temperature for the active element 18. Both the active element 18 and the reference element 16 are formed from an alloy wire of 90% platinum/10% iridium. Corresponding tests on prior art devices have yielded temperature excursions of over 60° C. at this same level of methane.

It will be appreciated that there are numerous implementations of the present invention which would be well known to one or ordinary skill. For example, the control circuit of the present invention could be implemented either with digital logic elements or in an analog format, in the latter case the comparators might be operational amplifiers driving the base terminal of a suitable transistor whose base/emitter path was connected between the power supply 32 and the gas sensor 14.

Although this invention has been shown and described with respect to a preferred embodiment, it will be understood by those skilled in this art that various changes in form and detail thereof may be made without departing from the spirit and scope of the claimed invention.

We claim:

1. A constant temperature catalytic gas detection instrument for measuring concentrations of an unknown gas, comprising:
   gas sensor means having a reference element and an active element, both of which are formed from a material having a resistivity that varies as a function of temperature;
   control means connected to said gas sensor means for sensing variations in the resistance of said active element and for regulating the current flowing through the active element to maintain the resistance of the active element relatively constant, and said control means responding to the presence of said unknown gas by causing the resistivity of said reference element to vary by regulating the current flow through the reference element as a function of the current flow through the active element;
   power supply means for supplying a source of operating potential; and
   indicator means connected to said gas sensor means for measuring a change in the difference between a potential across said reference element and a potential across said active element to provide an indication of the concentration of said unknown gas.

2. A constant temperature catalytic gas sensor according to claim 1, wherein said control means includes a driver means which is connected between said power supply and said gas sensor means for varying the operating potential presented to said gas sensor.

3. A constant temperature catalytic gas instrument according to claim 1, wherein said control means includes a first driver and a second driver, and wherein said first driver is connected between said power supply means and said active element of said gas sensor, and wherein said second driver is connected between said power supply means and said reference element of said gas sensor means.

4. A constant temperature catalytic gas instrument according to claim 3, wherein said first driver is controlled by a first comparator circuit which monitors current variations through said active element of said gas sensor means.

5. A constant temperature catalytic gas detection instrument according to claim 3, wherein said second driver includes a second comparator which acts to vary the resistance of said reference element as a function of the current flowing through said active element.

* * * * *